(12) United States Patent (10) Patent No.: US 8,979,852 B2
Taber et al. (45) Date of Patent: Mar. 17, 2015

(54) TOOLS FOR IMPLANTATION OF INTERSPINOUS IMPLANTS AND METHODS THEROF

(71) Applicant: Lanx, Inc., Broomfield, CO (US)

(72) Inventors: Justin Taber, Lafayette, CO (US);
Randall Mast, Denver, CO (US);
William Sandul, Broomfield, CO (US);
Andrew Lamborne, Golden, CO (US);
Michael Funk, Broomfield, CO (US)

(73) Assignee: Lanx, Inc., Broomfield, CO (US)

( * ) Notice: Subject to any disclaimer, the term of this patent is extended or adjusted under 35 U.S.C. 154(b) by 0 days.

(21) Appl. No.: 14/170,260

(22) Filed: Jan. 31, 2014

(65) Prior Publication Data

US 2014/0207198 A1 Jul. 24, 2014

Related U.S. Application Data

(62) Division of application No. 13/452,563, filed on Apr. 20, 2012, now Pat. No. 8,685,065.

(51) Int. Cl.
*A61B 17/88* (2006.01)
*A61B 17/70* (2006.01)

(52) U.S. Cl.
CPC ............. *A61B 17/88* (2013.01); *A61B 17/7068* (2013.01)
USPC ...................................................... 606/86 A

(58) Field of Classification Search
USPC .................. 606/246–249, 99, 104, 86 A, 86 B
See application file for complete search history.

(56) References Cited

U.S. PATENT DOCUMENTS

| 2003/0040746 A1 | 2/2003 | Mitchell et al. |
| 2008/0015609 A1 | 1/2008 | Trautwein et al. |
| 2011/0172711 A1 | 7/2011 | Kirschman |
| 2011/0319936 A1 | 12/2011 | Gordon et al. |

*Primary Examiner* — Pedro Philogene
*Assistant Examiner* — David Comstock
(74) *Attorney, Agent, or Firm* — Harness, Dickey

(57) ABSTRACT

The present disclosure provides a single insertion and compression instrument to facilitate the implantation of a spinous process implant, such as a spinous process fixation device, between and about adjacent spinous processes. The instrument has a first leg and a second leg, each with a handle and implant engaging portions. The implant engaging portions releasably couple to the spinous process implant and have compression pads to facilitate compression of fasteners on the plates into bone.

15 Claims, 10 Drawing Sheets

TOOLS FOR IMPLANTATION OF INTERSPINOUS IMPLANTS AND METHODS THEROF

CROSS-REFERENCE TO RELATED APPLICATIONS

This application is a divisional of U.S. patent application Ser. No. 13/452,563, which is related to U.S. patent application Ser. No. 11/934,604, filed Nov. 2, 2007, titled Spinous Process Implants and Associated Methods, now U.S. Pat. No. 8,241,330; U.S. patent application Ser. No. 12/020,282, filed Jan. 25, 2008, titled Spinal Implants and Methods; U.S. patent application Ser. No. 12/751,856, filed Mar. 31, 2010, titled Spinous Process Implants and Associated Methods; U.S. patent application Ser. No. 12/538,710, filed Aug. 10, 2009, titled Spinous Process Implants, Instruments, and Methods, now U.S. Pat. No. 8,382,801; and U.S. patent application Ser. No. 12/854,125, filed Aug. 10, 2010, titled Interspinous Implants and Methods, all of which are incorporated herein by reference as if set out in full.

FIELD

The present disclosure relates to tools that facilitate the implantation of interspinous process fusion implants and associated methods thereof.

BACKGROUND

The vertebrae of the human spine are arranged in a column with one vertebra on top of the next. An intervertebral disc lies between adjacent vertebrae to transmit force between the adjacent vertebrae and provide a cushion between them. The discs allow the spine to flex and twist. With age or injury, spinal discs begin to break down, or degenerate, resulting in the loss of fluid in the discs, and consequently, the discs become less flexible. Likewise, the discs become thinner allowing the vertebrae to move closer together. Degeneration also may result in tears or cracks in the outer layer, or annulus of the disc. The disc may begin to bulge outwardly. In more severe cases, the inner material of the disc, or nucleus, may actually extrude out of the disc. In addition to degenerative changes in the disc, the spine may undergo changes due to trauma from automobile accidents, falls, heavy lifting, and other activities. Furthermore, in a process known as spinal stenosis, the spinal canal narrows due to excessive bone growth, thickening of tissue in the canal (such as ligament), or both. In all of these conditions, the spaces through which the spinal cord and the spinal nerve roots pass may become narrowed leading to pressure on the nerve tissue which can cause pain, numbness, weakness, or even paralysis in various parts of the body. Finally, the facet joints between adjacent vertebrae may degenerate and cause localized and/or radiating pain. All of the above conditions, as well as others not specifically mentioned, are collectively referred to herein as spine disease.

Conventionally, surgeons treat spine disease by attempting to restore the normal spacing between adjacent vertebrae. This may be sufficient to relieve pressure from affected nerve tissue. However, it is often necessary to surgically remove disc material, bone, or other tissues that impinge on the nerve tissue and/or to debride the facet joints. Most often, the restoration of vertebral spacing is accomplished by inserting a rigid spacer made of bone, metal, or plastic into the disc space between the adjacent vertebrae and allowing the vertebrae to grow together, or fuse, into a single piece of bone. The vertebrae are typically stabilized during this fusion process with the use of bone plates and/or pedicle screws fastened to the adjacent vertebrae.

Although techniques for placing intervertebral spacers, plates, and pedicle screw fixation systems have become less invasive in recent years, they still require the placement of hardware deep within the surgical site adjacent to the spine. Recovery from such surgery can require several days of hospitalization and long, slow rehabilitation to normal activity levels.

Rather than spinal fusion, investigators have promoted the use of motion preservation implants and techniques in which adjacent vertebrae are permitted to move relative to one another. One such implant that has met with only limited success is the artificial disc implant. These typically include either a flexible material or a two-piece articulating joint inserted in the disc space. Another such implant is the spinous process spacer which is inserted between the posteriorly extending spinous processes of adjacent vertebrae to act as an extension stop and to maintain a minimum spacing between the spinous processes when the spine is in extension. The spinous process spacer allows the adjacent spinous processes to move apart as the spine is flexed. The extension stop spacers, however, also have had limited success.

Recently, the trend has been back towards fusion devices rather than motion preservation devices. One promising recent implant is a spinous process fusion plate. Similar to the fusion implants, the spinal process fusion plate promotes fusion between adjacent vertebrae to relieve pressure on the nerve. However, unlike more conventional spinal implant systems, the spinous process fusion plate facilitates less invasive procedures than conventional spinal fusion surgery. The need still exists for improved instruments to facilitate spinous process fusion plates.

BRIEF DESCRIPTION OF THE DRAWINGS

Various examples of the technology of the present application will be discussed with reference to the appended drawings. These drawings depict only illustrative examples of the technology described more fully herein and are not to be considered limiting of its scope.

DESCRIPTION OF THE ILLUSTRATIVE EXAMPLES

Figure 1:
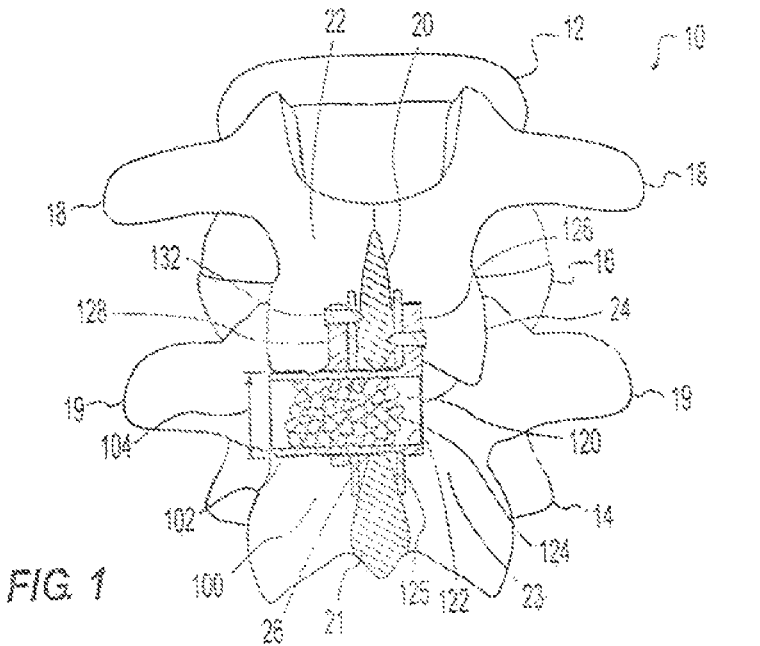
FIG. 1 is a posterior cross sectional view of an implant in situ that is deployed using a tool consistent with the technology of the present application.

The technology of the present application will be described in the context of spinal surgery, but one of ordinary skill in the art will recognize on reading the disclosure that the technology may be applicable to other medical fields. Moreover, the technology of the present application will be described with reference to certain exemplary embodiments. The word "exemplary" is used herein to mean "serving as an example, instance, or illustration." Any embodiment described herein whether or not specifically identified as "exemplary" is not to be construed as preferred or advantageous over other embodiments. Further, the instrument(s) described in accordance with, the technology of the present application facilitate surgical implantation of spinous process fusion plates. With that in mind, exemplary spinous process implants, according to the technology, may include a spacer and an extension extending outwardly from the spacer. The extension, which may be referred to as a wing, is sometimes described as being one or more lobes associated with the spacer. The spinous process implant may be configured for insertion between adjacent spinous processes of the cervical, thoracic, and/or lumbar spine. The spacer may be provided in a variety of sizes to accommodate anatomical variation amongst patients and varying degrees of space correction. The spacer may include openings to facilitate tissue in-growth to anchor the spacer to the vertebral bodies such as tissue in-growth from one or both of the spinous processes. The spacer may be configured for tissue in-growth from superior and inferior spinous processes to cause fusion of the adjacent spinous processes. The openings may be relatively large and/or communicate to a hollow interior of the spacer. A hollow interior may be configured to receive bone growth promoting substances such as by packing the substances into the hollow interior. The openings may be relatively small and/or comprise pores or interconnecting pores over at least a portion of the spacer surface. The openings may be filled with bone growth promoting substances. The spacer may further include a surface that facilitates bony ongrowth or ingrowth. The surface may include, for example, a titanium plasma spray coating, surface texturing, or the like.

The extension may extend transversely from the spacer relative to a spacer longitudinal axis to maintain the spacer between adjacent spinous processes. A single extension may extend in one or more directions or multiple extensions may be provided that extend in multiple directions. One or more extensions may be adjustable longitudinally relative to one another and/or the spacer to allow the extensions to be positioned laterally relative to the spinous processes. A moveable extension may be provided that is moveable axially relative to the spacer and another extension. Alternatively, a plurality of moveable extensions may be provided. For example, the extensions may clamp against the sides of the spinous processes to immobilize the spinous processes relative to one another and promote fusion between the adjacent vertebrae. The extensions may include fasteners engageable with the spinous processes. The fasteners may include sutures, wires, pins, straps, clamps, spikes, screws, teeth, adhesives, and/or other suitable fasteners. The fasteners may be integrated into the extensions or they may be modular. Modular fasteners may be adjustable, replaceable, and/or removable to allow tailoring of the kind and quality of fixation from rigid fixation to no fixation. The spacer, extensions, and/or fasteners may advantageously be made of different materials. For example, the spacer and extensions may be made of a relatively softer material while the fasteners may be made of a relatively harder material. For example, the spacer and/or extension may be made of a polymer and/or other relatively soft material and the fastener may be made of a metal and/or other relatively hard material.

Insertion of spinous process implants may be facilitated by a set of instruments alternately engageable with one another to increase the interspinous space and engageable with a spinous process implant as described in the related applications incorporated by reference. Some instrument sets may include different instrumentation for (1) placing or inserting the spinous process implant into the appropriate position and (2) compressing or translating one or both of the plates of the spinous process implant so they engage the adjacent spinous processes. Switching between instruments can either add time to the surgical procedure or require the hands of a second surgeon or assistant. The technology of the present application provides a single insertion and compression instrument. The single insertion and compression instrument moreover is hinged or articulated to allow for one or both extensions and/or the fasteners on the extensions (as explained further below) to angle in the coronal plane as needed. The single instrument to insert and compress the implant is configured to hold the implant assembled. The supraspinous ligament generally must be sacrificed to allow the insertion of the assembled implant to the interspinous space. The implant must provide sufficient clearance so that the fasteners on the plates cleat the spinous processes as the implant is inserted into the interspinous space from a generally posterior to anterior direction. Sufficient clearance is provided, for example, when the fastener(s) can be placed on opposite sides of a spinous process without cutting into or engaging the spinous process during the implant insertion. Once the implant is positioned, the compression of the handle causes the fasteners on the plate to bite into the spinous processes. The compressor may be hinged to allow for polyaxial orientation of the extension(s) or fasteners with respect to the spinous processes to facilitate differing sizes and thicknesses of the spinous processes as will be explained below.

Reference will now be made to FIGS. 1-9 describing an exemplary embodiment of a spinous process implant for which the instruments of the present application may be used. While a specific exemplary embodiment is provided herein, implants associated with any of the incorporated applications or similar spinous process fusion plates may benefit from the technology of the present application.

Figure 2:
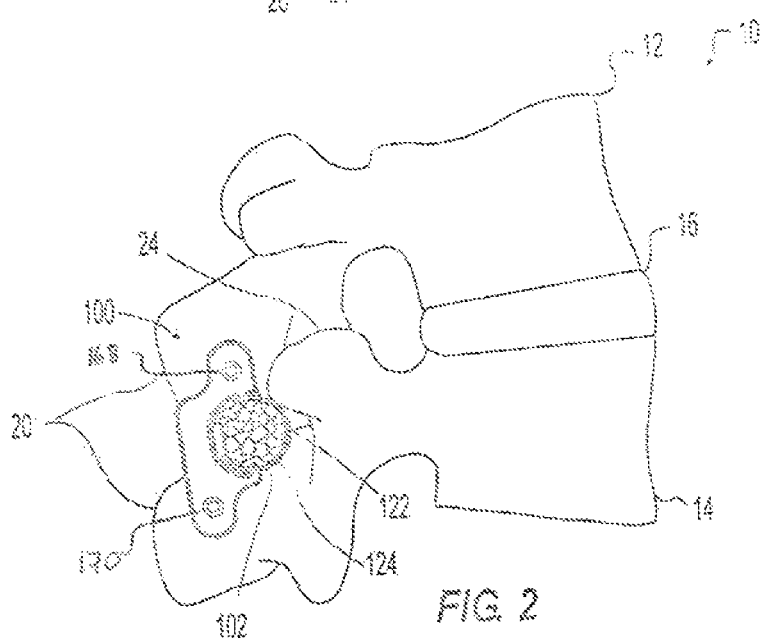
FIG. 2 is a side elevational view of the implant of FIG. 1 in situ.

FIGS. 1 and 2 depict posterior and lateral views of a pair of adjacent vertebrae of the lumbar spine 10. A superior vertebra 12 is separated from an inferior vertebra 14 by a disc 16. Each vertebra includes a pair of transverse processes 18, 19, a posteriorly projecting spinous process 20, 21, and a pair of lamina 22, 23 connecting the transverse processes 18, 19 to the spinous process 20, 21. In addition to the connection through the disc 16, the vertebrae 12, 14 articulate at a pair of facet joints 24.

FIGS. 1-9 illustrate an exemplary spinous process implant 100. The implant 100 includes a spacer 102 positioned between the spinous processes 20, 21. The geometry of the implant 100 is illustrated with the use of axes that define length (l), height (h), and width (w) directions for the spacer. When implant 100 is implanted in a patient, the height direction of the spacer 102 is generally oriented along the superior/inferior direction of the patient's anatomy, the width direction of the spacer 102 is generally oriented along the anterior/posterior direction of the patient's anatomy, and the length direction of the spacer 102 is generally oriented along the lateral/medial direction of the patient's anatomy.

The height 104 (FIG. 1) of spacer 102 limits how closely the spinous processes 20, 21 can move together. As the implant in this example is a fusion plate, the height also limits how distantly the spinous processes 20, 21 can move apart. Thus, the spacer 102 maintains a minimum and maximum distance between the spinous processes 20, 21. In the case of spine disease involving posterior subsidence of the adjacent vertebra, insertion of the spacer 102 between the spinous processes 20, 21 will move the vertebrae apart and relieve pressure on nerve tissue and the facet joints 24.

Figure 3:
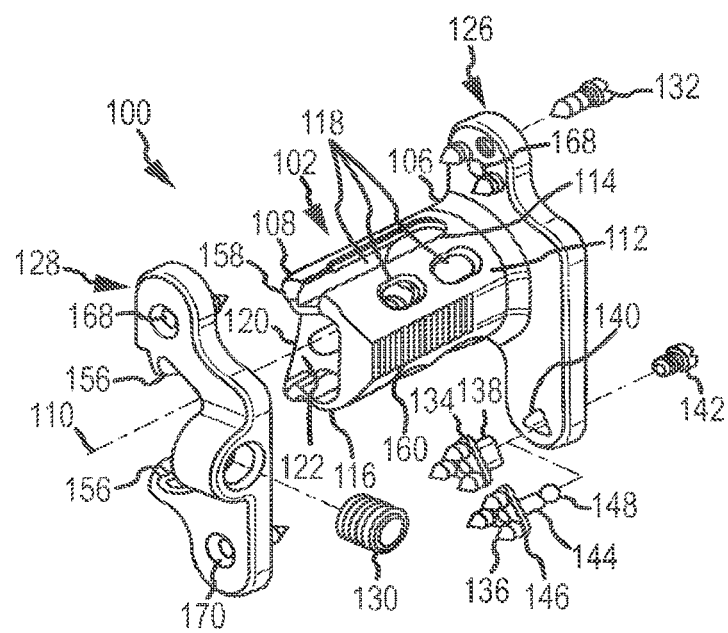
FIG. 3 is a an exploded perspective view of the implant of FIG. 1.

As shown in FIG. 3, the spacer 102 includes a first end 106, a second end 108, and a longitudinal axis 110 extending from the first end to the second end. The spacer 102 has a sidewall 112, generally parallel to the longitudinal axis 110, including superior and inferior outer surfaces 114, 116. Transverse openings 118 (see also FIG. 6) communicate from the superior and inferior outer surfaces 114, 116 inwardly to facilitate tissue in-growth. The exemplary spacer 102 includes a hollow interior 120 bounded by an inner surface 122 such that the openings 118 communicate from the outer surfaces 114, 116 to the hollow interior 120. Bone growth promoting substances 124 are shown packed into the hollow interior 120 in FIGS. 1 and 2 to promote fusion of the vertebrae 12, 14 by bone growth between the spinous processes 20, 21.

The spinous process implant 100 further includes a first extension 126 projecting outwardly from the spacer 102 along the spacer height direction h and transversely to the longitudinal axis 110 to lie generally alongside the superior and inferior spinous processes 20, 21. Abutment of the first extension 126 with the spinous processes 20, 21 helps prevent lateral movement of spacer 102, thereby maintaining spacer 102 between the spinous processes 20, 21. In the exemplary spinous process implant 100, the first extension 126 is fixed relative to the spacer 102 and the implant includes a second extension 128 mountable to the spacer for axial movement relative to the first extension 126. The second extension 128 may be moved toward the first extension 126 to approximate the width of the spinous processes 20, 21 and better stabilize the implant 100. It is fixed in place by tightening a set screw 130 (FIG. 3) against the spacer 102. The extensions 126, 128 include fasteners 132, 134, 136 projecting from the extensions 126, 128 to engage the spinous processes 20, 21 to fix the spacer 102 to the spinous processes 20, 21. FIG. 1 depicts an additional bone growth promoting substance in the form of strips of bone 125 sandwiched between the extensions 126, 128 along the sides of the spinous processes 20, 21 to promote bone growth along the sides of the spinous processes to further enhance fusion of the vertebrae 12, 14. The extensions 126, 128 preferably extend inferiorly as well as superiorly from spacer 102 to optionally attach to the inferior spinous processes to immobilize the spinous processes 20, 21 relative to one another while fusion takes place.

Fasteners 132, 134, and 136 may take any suitable form. They may be made integral with the extensions 126, 128 such as by machining or casting them with the extensions or they may be formed separately and permanently attached to the extensions 126, 128. Fastener 132 is a sharpened spike that threadably engages the extension 126. The threaded engagement allows the fastener 132 to be replaced with a different fastener 132. For example, the fastener 132 may be replaced by one that has a different shape, a different size, a different material, or a different surface coating. The threaded engagement also allows the fastener 132 to be adjusted to extend by varying amounts from the extension 126 to vary how it engages the bone. Thus, the fastener 132 can be adjusted to fit differently shaped bones or to penetrate into a bone by varying amounts. For example, multiple threaded fasteners 132 can be adjusted to extend by different amounts to conform to curved or angled bone. Finally, the threaded engagement allows the user to remove the fastener 132 when fixation is not desired such as when it is desired to use implant 100 in a non-fusion procedure as an extension stop without limiting flexion.

As best seen in FIG. 3, fasteners 134 and 136 are provided as multi-spike pods allowing a plurality of spikes to be quickly adjusted, changed, or omitted. Fastener 134 includes a non-circular tab 138 engageable with a non-circular opening 140 in the extension 126. The non-circular engagement prevents the fastener 134 from rotating. The tab 138 may form a press-fit, snap-fit, or other suitable engagement with the opening 140. The tab 138 may be further secured by a supplemental screw 142. Fastener 136 includes a threaded shaft 144 threadably engaged with a base member 146 to allow the length of the fastener 136 to be adjusted. The shaft 144 engages the extension 126 in a rotating and pivoting manner such that the fastener 136 can be adjusted rotationally and angularly to engage the bone surface. In the illustrative embodiment, the shaft 144 terminates in a spherical ball 148 that engages the opening 140 in a ball-and-socket arrangement for three degrees of freedom. However, any mechanism that allows any number of degrees of freedom may be used. The fastener 136 may be allowed to move in use so that as the extension 126 is pressed toward a bone, the fastener 136 adjusts to the angle of the bone surface. The fastener 136 also may be secured such as by screw 142 to adjust the tension in the joint and/or to lock the fastener 136 in a predetermined orientation.

Figure 4:
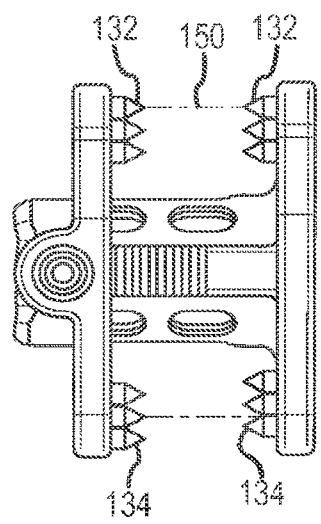
FIG. 4 is a posterior elevational view of similar alternatives of the implant of FIG. 1.

FIG. 4 illustrates the axial relationship of fasteners on the opposing extensions 126, 128. In the illustrative implant 100, the fasteners 132 at the top of the implant 100 are shown aligned along a common axis 150 that is substantially perpendicular to extensions 126 and 128. The fasteners 134 at the bottom of the implant 100 are shown offset so that they can interleave, if necessary, as they are pressed into a bone. Any combination of fastener type, number, and alignment may be provided on the implant 100.

Figure 5:
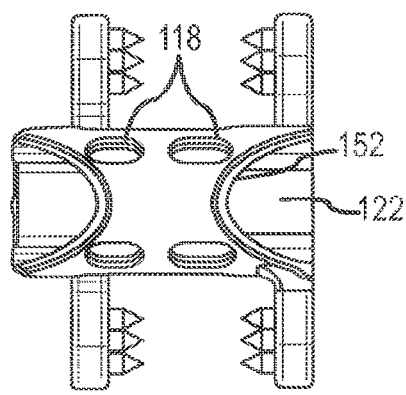
FIG. 5 is an anterior elevational view of the implant of FIG. 1.
Figure 6:
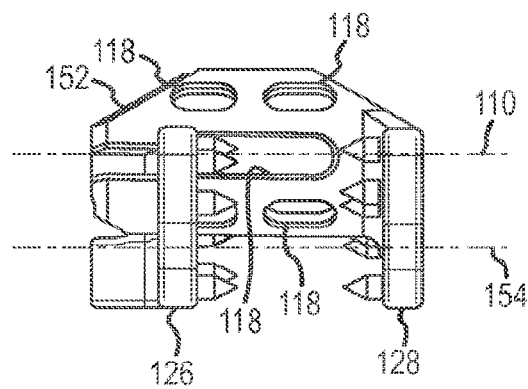
FIG. 6 is a top plan view of the implant of FIG. 1.

As seen in FIGS. 5 and 6, the ends 106, 108 of the spacer 102 include anterior chamfers 152. These chamfers 152 allow the ends 106, 108 to clear posteriorly facing structures of the vertebrae 12, 14 such as the facet joints 24. Also, as seen in FIGS. 5 and 6, the spacer 102 is offset anteriorly (in the spacer width direction w) relative to the extensions 126, 128 such that the longitudinal axis 110 of the spacer 102 is anterior of a midline plane 154 (FIGS. 6, 8) of the extensions 126, 128. The anterior offset of the spacer 102 allows it to fit deeply between the spinous processes 20, 21 while the extensions 126, 128 fit alongside the spinous processes 20, 21.

Figure 7:
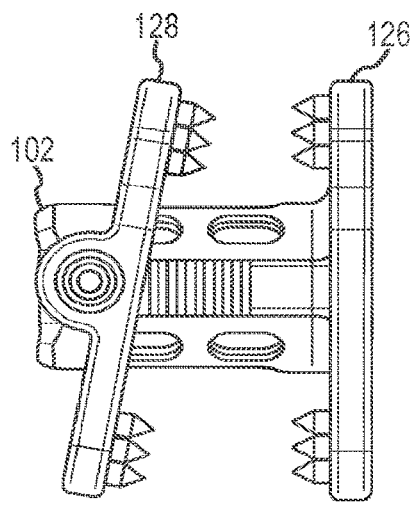
FIG. 7 is a posterior elevational view of the implant of FIG. 1 showing the assembly in an alternate position.
Figure 8:
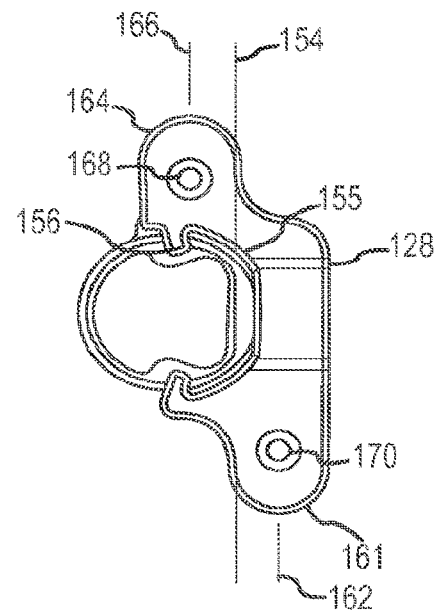
FIG. 8 is a side elevational view of the implant of FIG. 1.

As best seen in FIGS. 3 and 8, the second extension 128 defines an aperture 155 conforming generally to the cross-sectional shape of the spacer 102. In the illustrative embodiment of FIGS. 1-9, the aperture 155 opens anteriorly to form a "C"-shape. Tabs 156 extend inwardly from the superior and inferior portions of the aperture to slidingly engage elongated slots 158 in the superior and inferior surfaces of the spacer 102. The second extension 128 can be translated longitudinally along the spacer length l toward and away from the first extension 126. Tightening the set screw 130 against the posterior side 160 of the spacer 102 forces the tabs 156 posteriorly against the sides of the slots 158 and locks the second extension 128 in place longitudinally. The posterior side 160 of the spacer 102 may be roughened as shown to better grip the set screw 130. The set screw 130 may also dig into the surface of the spacer 102 upon tightening to positively grip the spacer 102. The aperture 155 (FIGS. 3, 8) may conform closely to the spacer 102 to constrain the second extension 128 to generally parallel motion relative to the first extension 126. Alternatively, the aperture 155 may be larger than the spacer 102 by a predetermined amount to permit a predetermined amount of angular adjustment of the second extension 128 relative to the first extension 126 as shown in FIG. 7 to allow the extension 128 to adjust to the underlying bone surface. In alternative embodiments, second extension 128 is generally "O" shaped instead of "C" shaped such that the aperture surrounds the spacer. In this manner, spacer 102 slides completely within aperture 155. In these embodiments, second extension 128 may include a single tab 156 which engages a single slot 158 within spacer 102. Alternatively, two or more tabs 156 may be used, extending inwardly into aperture 155 at desired locations to engage corresponding slots 158. It will be appreciated that generally "O" shaped apertures include any shape of aperture into which spacer 102 is received whereby the structure of second extension 128 surrounds spacer 102 and permits translation of second extension 128 along spacer 102.

Figure 9:
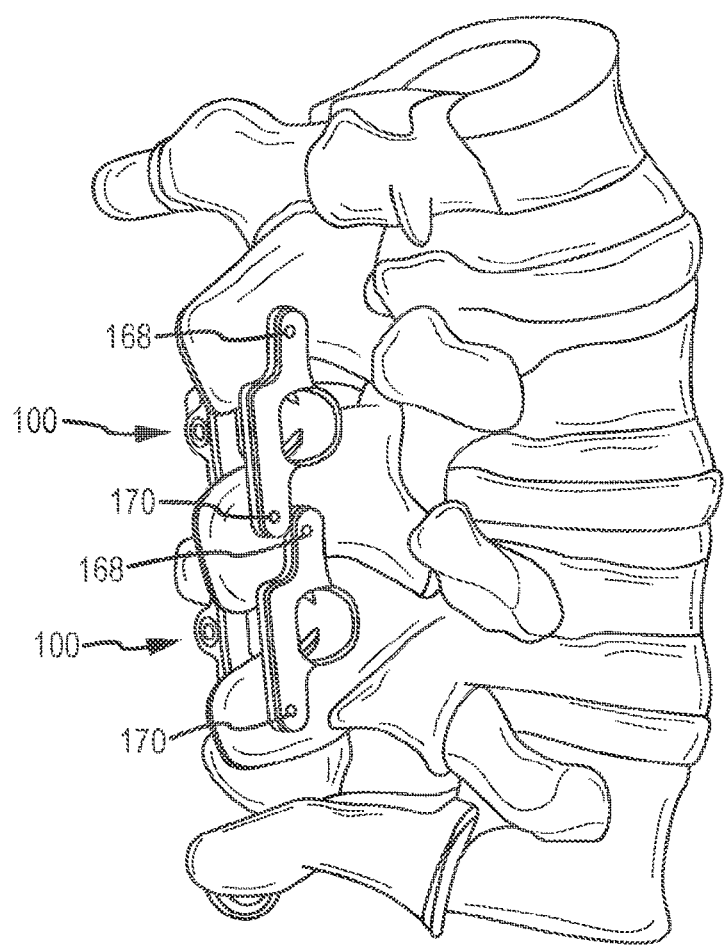
FIG. 9 is a perspective view of a pair of implants like that of FIG. 1 in situ.

As best seen in FIG. 8, the second extension 128 includes a first inferior lobe 161 having a first lobe centerline 162 and a second superior lobe 164 having a second lobe centerline 166. In the illustrative embodiment, the first lobe centerline 162 and the second lobe centerline 166 are parallel and spaced apart so that the second extension 128 has a generally "Z"-shaped plan form. This shape allows the extension of one implant 100 to interleave, if necessary, with another implant 100 in a multilevel surgery (as shown in FIG. 9) to permit close spacing of the implants, and/or longer extension lobes for more extensive bone engagement. In addition, first inferior lobe 161 has a semi-circular convex shape that is generally complementary to a semi-circular superior concave surface 165 formed adjacent second superior lobe 164. Similarly, second superior lobe 164 has a semi-circular convex shape that is generally complementary in shape to a semi-circular inferior concave surface 163 formed adjacent first inferior lobe 161. As indicated in FIG. 8, first inferior lobe 161 is adjacent to inferior concave surface 163, and extension midline plane 154 is located between first inferior lobe 161 and inferior concave surface 163. Second superior lobe 164 is adjacent superior concave surface 165, and extension midline plane 154 is located between second superior lobe 164 and superior concave surface 165. Moreover, first inferior lobe radius $r_1$ is substantially equal to superior concave surface, radius $r_4$, while second superior lobe radius $r_3$ is substantially equal to inferior concave surface, radius $r_2$. As a result, when two implants are placed on adjacent spinal levels, the first inferior lobe 161 of the upper implant may be (but need not be, depending on what is medically indicated) interfitted into the superior concave surface 165 of the inferior implant. In addition, the second superior lobe 164 of the inferior implant may be interfitted into the inferior concave surface 163 of the superior implant. In the illustrative example of FIGS. 1-9, first inferior lobe 161 and second superior lobe 164 form a unitary second extension 128. Although not separately depicted, first extension 126 also has complementary lobes that are similarly configured and oriented relative to one another.

As shown in FIG. 9, multiple spinous process implants 100 may be placed on adjacent levels of the spine. As illustrated in the figure, a first superior implant 100 is positioned with its spacer 102 between a first superior spinous process and a second intermediate spinous process, while a second inferior implant 100 is positioned with its spacer 102 between the second intermediate spinous process and a third inferior spinous process. The first extensions 126 of the superior and inferior implants are located on a first side of the patient's sagittal plane, while the second extensions 128 of the superior and inferior implants are located on a second side of the patient's sagittal plane.

In the illustrative embodiment of FIGS. 1-9, the extension lobe centerlines 162,166 are offset equidistantly from the midline plane 154 of the second extension 128. Although not separately shown, the first extension 126 is configured similarly. The centerlines 162, 166 may vary from parallel and they may be offset asymmetrically to form different shapes to accommodate different vertebral anatomy. For example, the shape may be tailored for different portions of the spine 10. In the illustrative embodiment of FIGS. 1-9, the first extension 126 has the same shape as the second extension 128. However, the shape may be varied between the first and second extensions 126, 128.

As shown in for example, FIGS. 2, 3, 8, and 9, the first extension 126 and second extension 128 may have tool connection points 168 and 170. The tool connection points 168 and 170 are shown as dimples or bores in the exemplary embodiment and are cooperatively shaped to engage an associated prong, tab or protrusion on the insertion/compression instrument as will be explained further below.

Figure 10:
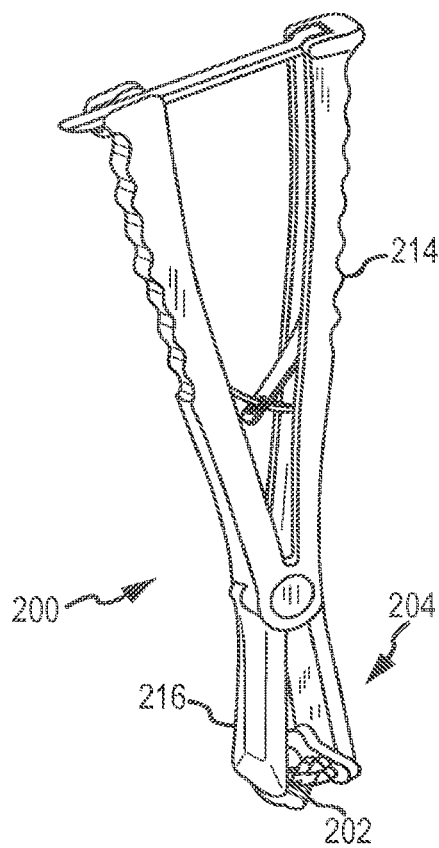
FIG. 10 is a perspective view of an instrument consistent with the technology of the present application shown with an implant in the open or insertion position.
Figure 11:
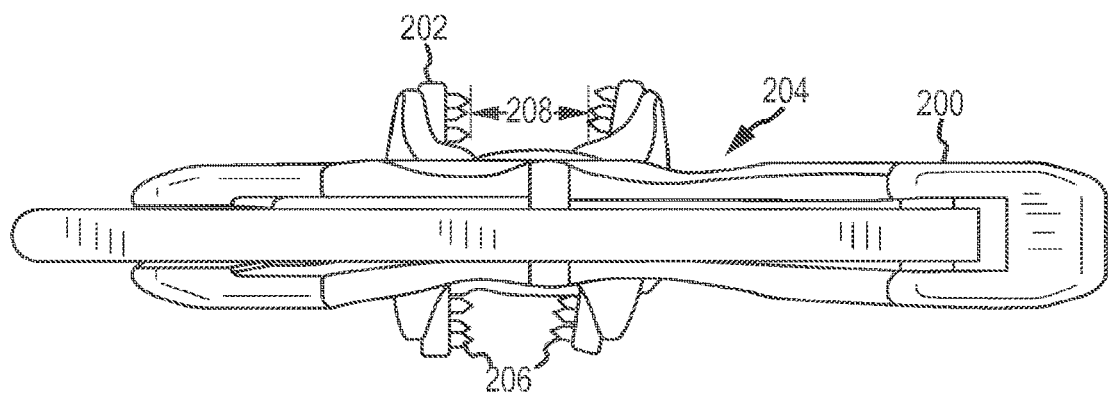
FIG. 11 is a view of the instrument of FIG. 10 in a more open configuration.
Figure 12:
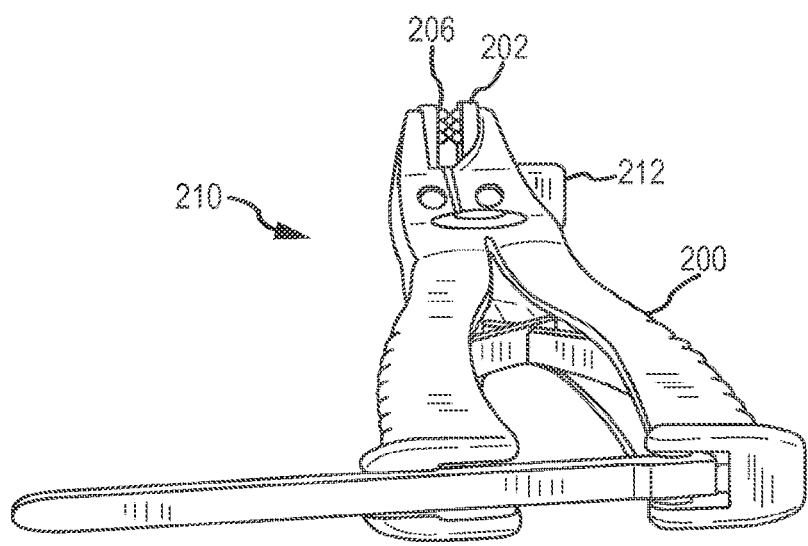
FIG. 12 is a view of the instrument of FIG. 10 where the instrument and implant are shown in the closed or clamped position.

FIGS. 10, 11, and 12 depict an instrument 200 that is releasably coupled to an implant 202, such as the above described implant 100. FIGS. 10 and 11 show views of the instrument 200 and implant 202 in various open (or insertion) positions 204. As better seen in FIG. 11, the fasteners 206, which may include fasteners such as the above described fasteners 132, 134, and 136, are separated by a distance 208. The distance 208 extends in the medial/lateral direction of the spinous process or length direction of the implant 202. The distance 208 provides sufficient clearance for the implant to be inserted into the interspinous space as shown in FIG. 1 from a posterior to anterior direction. In this manner, the fasteners 206 may be positioned on one or both sides of a spinous process. Because in FIGS. 10 and 11 the first and second implant extensions are assembled, the implant 202 may not be implanted laterally or anteriorly. FIG. 12 shows the instrument 200 and implant 202 in the closed or clamped position 210. The fasteners 206 in the closed or clamped position would bite into the spinous process to fix the first, the second or both extensions of the implant 202 to the spinous process. The spacer 212 of the implant 202 is shown extending from one side of the instrument 200. The instrument 200 may generally be considered to have a handle portion 214 and an implant portion 216. The handle portion 214 and the implant portion 216 are operatively connected such that compressing handle portion 214 causes implant portion 216 to compress the implant 202 such that the fasteners bite into bone, such as the spinous process or other applicable bone.

Figure 14:
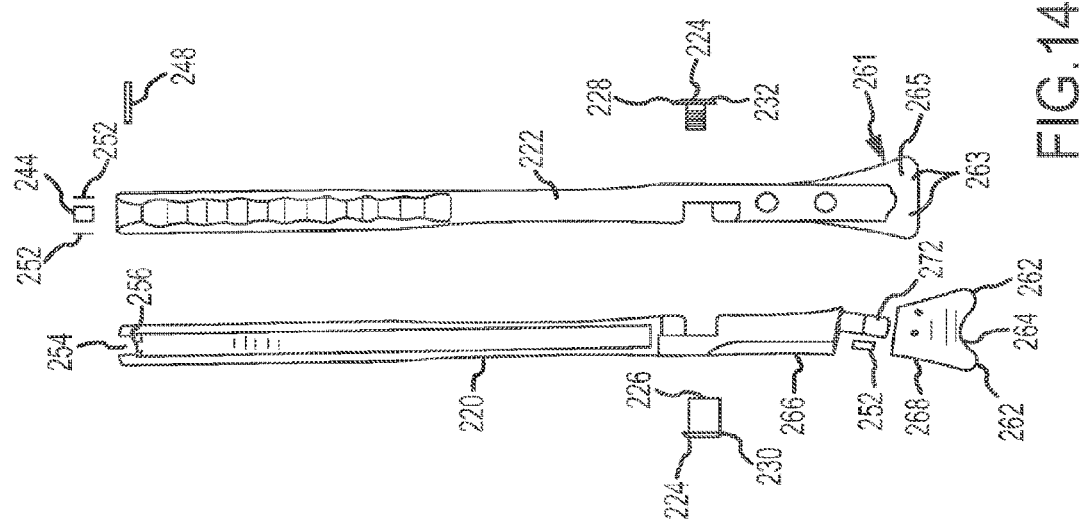
FIG. 14 is another elevation view of the instrument of FIG. 10 partially exploded.
Figure 13:
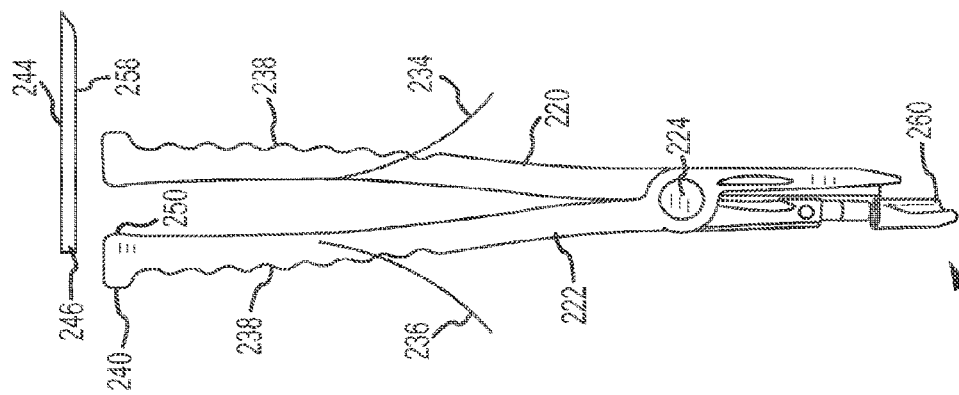
FIG. 13 is an elevation view of the instrument of FIG. 10.

With reference to FIGS. 13 and 14, the instrument 200 will be explained in more detail. FIGS. 13 and 14 show partially assembled views of the instrument 200. The instrument 200 comprises a first leg 220 pivotally coupled to a second leg 222. The first leg 220 is pivotally coupled to second leg 222 by any conventional mechanism, such as, for example, a hinge formed by a post 224. The post 224 may be a female type post having a socket 226 to cooperatively engage a male post 228 such that the female post 224 and male post 228 join to form an axle allowing pivotal movement. The female post has a flanged surface 230 opposite the socket and the male post 226 has a head or flanged surface 232 that cooperatively holds the instrument 200 together and allows for pivotal movement of the first and second legs 220, 222. The posts 224 and 228 may be contained in countersunk bores. Alternatively, a single post 224 may pivotally couple the first and second legs 220, 222. In this case, the single post 224 would have flanged surfaces 230 on opposing sides of the post 224. The first and second legs 220, 222 are biased towards the open position by interleaved female and male springs 234, 236 coupled to first and second legs 220, 222 respectively. Female and male springs 234, 236 may be coupled to first and second legs 220, 222 in a conventional manner including, for example, using spring screws 238.

The instrument 200 has a proximal end 240 and a distal end 242. The proximal ends 240 of the first and second legs 220, 222 are coupled by a ratchet 244. The ratchet 244 is pivotally coupled to one of the first and second legs 220, 222. In this exemplary embodiment, the ratchet 244 is pivotally coupled to the proximal end 240 of the second leg 222. The ratchet 244 may be pivotally coupled to the second leg 222 by a pin 248 extending through a bore 246 in the ratchet 244 and a corresponding bore 250 in the second leg 222. The pin 248 provides an axis about which the ratchet may be moved between a locked position and an unlocked position. Optionally, washers 252 may be positioned between the ratchet 244 and the second leg 222 to facilitate pivotal motion. The ratchet 244 is movably and selectively coupled to the proximal end 240 of the first leg 220 as well. The first leg 220 at the proximal end forms a channel 254 through which the ratchet 244 may move. A protrusion 256 extends into the channel 254 and releasably couples to striations 258 formed on at least one side of ratchet 244. Thus, as first and second legs 220, 222 are compressed against the female and male springs 234, 236, the striations 258 of ratchet 244 couples to the protrusion 256 in channel 254 to prevent the legs from decompressing when the grip is released. If ratchet 244 is pivoted with respect to the leg 222, the female and male springs 234, 236 will decompress the handles.

The distal end 242 of first leg 220 includes a member 260 that is releasably coupled to an extension. For example, the member 260, as will be explained further below, releasably couples to second extension 128 (FIG. 3). The member 260 terminates in compression pads 262 that allow an even distribution of clamping force to cause the fasteners of second extension 128 to bite into the bone. The compression pads 262 also provide a cavity 264 therebetween that allows the spacer body 212 of the implant 202 to extend beyond the member 260 as the second extension 128 is moved closer to the first extension. Correspondingly, second leg 222 has a member 261 at the distal end 242 to releasably couple to the first extension 126 (FIG. 3) As can be appreciated, compression of first and second legs 220, 222 at the proximal end 240 causes compression of the distal end 242 causing the second extension 128 to translate over spacer 102 (FIG. 3) such that second extension 128 moves relatively closer to first extension 126. However, both the first and second extensions 126, 128 move relative to the bone or spinous process such that the fasteners on each extension bite into the bone.

Similarly, the distal end 242 of the second leg 222 includes a member 261 that is releasably coupled to an extension. For example, the member 261, as will be explained further below, releasably couples to first extension 126 (FIG. 3). The member 261 terminates in compression pads 263 that allow an even distribution of clamping force to cause the fasteners of first extension 126 to bite into the bone. In this exemplary configuration, the spacer 102 is unitary with first extension 126. Thus, first extension 126 does not move with respect to the spacer 102. The member 261 has a midline compression span 265 extending between the compression pads 263. The midline compression span 265 facilitates the compression of second extension 128 over the sidewall of the spacer 102 in this configuration. For configurations where both the first and second extensions move relative to the spacer body, the midline compression span 265 may be replaced with a cavity similar to cavity 264.

Figure 15:
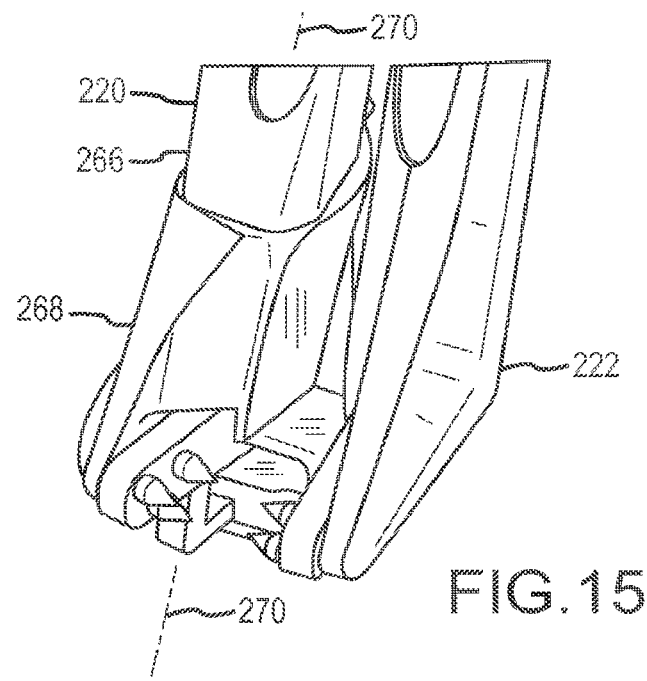
FIG. 15 is a perspective view of the distal end of the instrument of FIG. 10.
Figure 16:
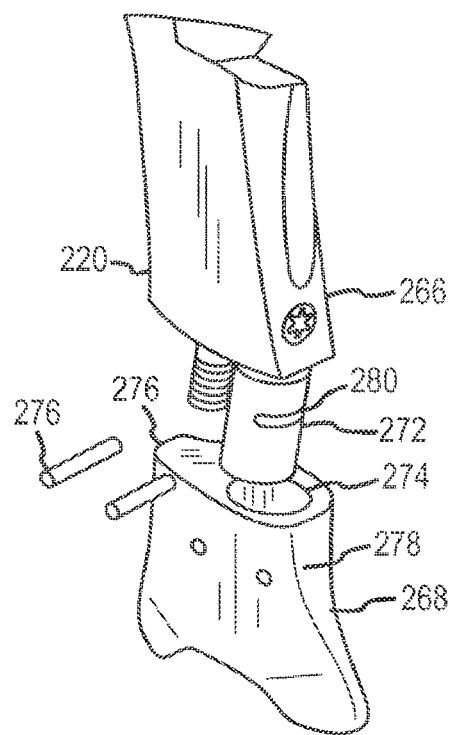
FIG. 16 is a perspective view of the distal end of one of the legs of the instrument of FIG. 10 partially exploded.

With reference to FIG. 7, the implant 100 is shown where the second extension 128 is pivoted with respect to the first extension 126. The pivoting of the second extension 128 with respect to the first extension 126 allows, among other things, the accommodation of differing anatomy. To allow for the second extension 128 to be pivoted with respect to first extension 126, the implant portion 242 of first leg 220 is formed into two parts comprising a stationary instrument part 266 and a pivotal implant part 268, shown partially exploded in FIG. 14, and pivoted about an axis 270 in FIG. 15. To couple the stationary instrument part 266 to pivotal implant part 268, an axle 272 extends from the distal end of the stationary instrument part 266 to cooperatively engage a bore 274 in the pivotal implant part 268. The pivotal implant part 268 rotates about the axle 272 to allow for pivotal movement of the pivotal implant part 268. The pivotal implant part 268 is coupled to the axle 272 by any conventional means. One possible connection includes a pair of connection pins 276 extending through a corresponding pair of connecting bores 278 such that the pins engage channels 280 forming a tongue and groove connection between the pivotal implant part 268 and the axle 272. A compression spring 282 is provided between the stationary instrument part 266 and the pivotal implant part 268 to place the two pieces in tension such that the parts are rotational, but locked. The above is one exemplary connection allowing pivotal freedom between the stationary instrument part 266 and the pivotal implant part 268. Other connections may similarly be implemented such as styles of a ball and socket joint, a cardan joint, a universal joint, a gimbal joint, a flexible connection (such as, for example, a metal spring connection), or the like may provide for the pivotal relationship as well. In still other embodiments, rather than provide an axle 272, the legs may be formed cylindrically such that the member 261 may clamp, such as, for example, a C-clamp to the leg and pivot about the cylindrical leg.

In certain embodiments, the distal end 242 of the instrument 200 may comprise pins, forks, prongs, or other fasteners to releasably connect the instrument 200 to, for example, the tool connection points 168, 170 on the implant. In other configurations, however, the instrument 200 may provide a spring clamp to grasp the extensions, such as, for example, the extensions 126 and 128 described above with respect to FIGS. 1-9.

Figure 17:
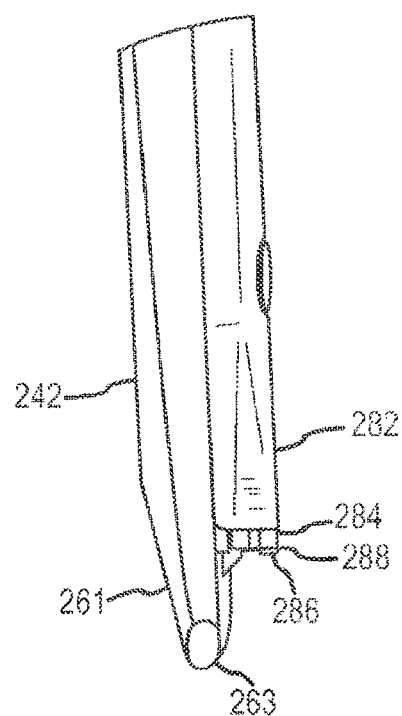
FIG. 17 is a view of the distal end of the other leg of the instrument of FIG. 10.
Figure 18:
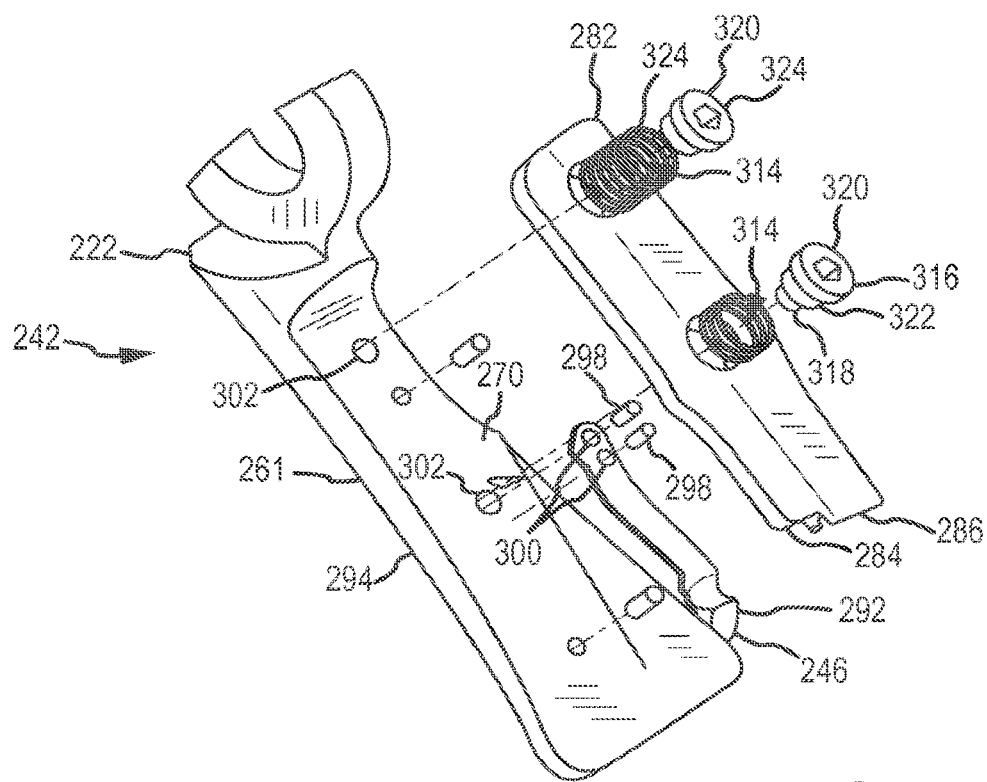
FIG. 18 is a partially exploded perspective view of the distal end of the other leg of the instrument of FIG. 10.

With reference to FIGS. 17 and 18, the distal end 242 of the second leg 222 of instrument 200 is shown in a configuration that provides for a spring clamp. The member 261 terminates in compression pads 263. A clamp 282 is coupled to member 261. An end 284 of the clamp 282 comprises a ridge 286 that forms a cavity 288 between the member 261, the end 284 of the clamp 282, and the ridge 286. The cavity 288 is sized to cooperatively and releasably engage first extension 126, in this exemplary embodiment.

The connection of clamp 282 to the member 261 is explained in further detail with respect to FIG. 18 that provides an exploded view of the distal end 242 of the second leg 222. As can be appreciated, any number of conventional mechanisms may be used to align the clamp 282 with the member 261. Alignment pins and alignment detents are shown in this exemplary embodiment. The member 261 includes a slot 290 adapted to fit a slot spring 292. The slot spring 292 resides in the slot 290 and is coupled to the member 261 at a first end 294 and movable at a second end 296. The second end 296 is opposite the ridge 286. The second end 296 of the slot spring 292 and the ridge 286 cooperate to grasp the first extension 126 of the exemplary implant 100 described above when the first extension 126 fits in cavity 288. The slot spring 292 may be coupled to the member 261 by a pair of spring pins 298 extending through spring bores 300 and clamped between member 261 and clamp 282.

Figure 19:
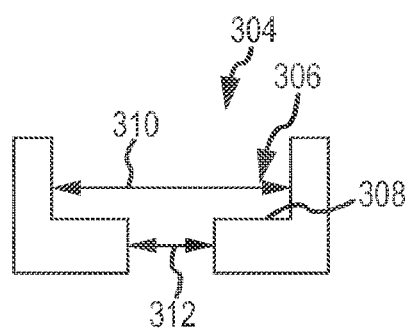
FIG. 19 is a cross-sectional view of a bore of the clamp of FIG. 18.

The member 261 has a plurality of bores 302 which, in this exemplary embodiment, are threaded bores. The clamp 282 has a plurality of bores 304 aligned with bores 302. The bores 304 have countersunk regions 306 terminating in a shoulder 308 internal to the bores 304. As best seen in the cross-sectional view of FIG. 19, the bores 3104 have a first diameter 310 and a second diameter 312 where the second diameter 312 is smaller than the first diameter 310. A compression spring 314, such as a helical or disc spring, fits in each of the bores 304. The spring 314 has an internal diameter larger than second diameter 312 and an external diameter smaller than first diameter 310. A fastener 316 also fits into each bore 304. The fastener 316 includes a shaft 318 that cooperatively engages bore 302, such as, for example, corresponding threads in bore 302 and on shaft 318. The fastener 316 also includes a head 320. The head 320 has a diameter larger than second diameter 312 and less than diameter 310. The head 320 has a compression surface 322 that engages a top 324 of compression spring 314. The head 320 also includes a tool port 324 to cooperatively engage a tool, such as a hex driver as shown, such that fastener 316 may be threaded into bore 302. Threading the fastener 316 causes the compression surface 322 of head 320 to engage the top 324 of compression spring 314 and compress the spring 314 towards shoulder 308.

The compression springs 314 and the slot spring 292 maintain the cavity 288 such that introduction of the extension of implant 100 to cavity 288 causes the cavity to expand against the springs and accept the extension. The compression springs 314 and the slot spring 292 provide seating force to capture the extension in the cavity 288. To facilitate introducing the extension to cavity 288, one or both of slot spring 292 and ridge 286 may be tapered or chamfered. While the clamping force provided by the compression springs 314 and the slot spring 292 is sufficient to grasp extensions of implant 100, the clamping force also must be such as to allow for the removable of the instrument 200 after the implant is clamped onto the bone.

While not specifically shown, the pivotal implant part 268 may have a similar structure providing a clamp with cooperative springs to grasp the second extension 128. However, the implant does not need to be coupled to each leg in the same fashion.

One advantage of the technology of the present application is the ability for the instrument 200 to allow for a relatively small or minimal incision and surgical area for insertion of the spinous process fusion plates; an example of which is shown in FIGS. 1-9. The surgeon using the instrument 200 would size the implant to be used in a conventional manner after making a single incision, which would be a midline incision. Tissue and bone removal also would be accomplished in a conventional manner to prepare the site for the implant. As will be appreciated, using the instrument 200 may require the sacrifice of spinous ligaments including, for example, the supraspinous ligament. The implant 100 is coupled to the instrument 200 while the instrument is in the open position 204. In the open position, the fastener tips are separated by a sufficient distance to allow the implant first extension and second extension (along with the applicable fasteners) to be inserted in a posterior/anterior direction relative to the patient past the spinous processes. In exemplary embodiments, the implant second extension is engaged or mated with the spacer prior to attaching the implant to instrument 200. Alternatively, the implant second extension is engaged or mated with the spacer after attaching the implant to instrument 200, but prior to insertion of the implant between adjacent spinous processes. In this manner, the instrument 200 maintains the mated orientation of the implant during insertion between two adjacent vertebrae. In an alternative embodiment, instrument 200 may be opened or closed with implant portions attached, with the alignment of the first and second legs allowing the implant portions to engage and disengage from each other as desired.

Moreover, the spacer 102/212 is moved into position between the adjacent spinous process. Once the spacer 102/212 is positioned and the extensions 126, 128 (or wings) are placed using the instrument, the handle portion 214 of first and second legs 220, 222 are compressed causing the implant portion 216 to compress and move the extensions and fasteners of the implant toward the bone, which, in this case, are the adjacent spinous processes. While compressing the handle portion 216, the ratchet 244 maintains the compression against male and female spring bias. Once sufficiently seated, the ratchet 244 is pivoted to release the compression aid the instrument is removed leaving the implant in place, properly aligned with the adjacent spinous processes, and the fasteners properly seated into the bone.

Implants and instruments of the present disclosure may be used alone, or in conjunction with other implants and instruments. In one embodiment, an interbody device is implanted in a patient during a lateral procedure. In this procedure, the patient is placed on their side for a lateral approach to the spine to deliver the interbody between two adjacent vertebrae. Once the interbody is placed, supplemental fixation devices may be applied to the patient to further stabilize the spinal segment to be fused. In a particular embodiment, the patient remains on their side and implant 100 is inserted using instrument 200. In this manner, a single instrument 200 may be used to both insert and compress implant 100 across adjacent spinous processes to provide supplemental fixation at the treated spinal segment. The use of a single tool 200 allows the surgeon to more easily provide supplemental fixation without the need to reposition the patient, and without multiple tools extending from the surgical site.

Although examples of a spinous process implant and associated instruments and techniques have been described and illustrated in detail, it is to be understood that the same is intended by way of illustration and example only and is not to be taken by way of limitation. Accordingly, variations in and modifications to the spinous process implant, instruments, and technique will be apparent to those of ordinary skill in the art, and the following claims are intended to cover all such modifications and equivalents.

We claim:

1. A single instrument for inserting and compressing a spinous process implant, the instrument comprising:
   a first leg, the first leg comprising a first handle portion and a first implant engaging portion;
   the first implant engaging portion comprising:
   a stationary instrument part, and
   a pivotal implant part, wherein the pivotal implant part pivots relative to the stationary instrument part in at least one plane about a first axis; and
   a second leg, the second leg comprising a second handle portion and a second implant engaging portion, the second leg pivotally coupled to the first leg for pivotal movement about a second axis transverse to the first axis at a pivot point between the first and second handle portions and the first and second implant engaging portions such that compression of the first and second handle portions causes compression of the first and second implant engaging portions;
   wherein the first and second implant engaging portions are adapted to couple to an implant and insert a first portion of the implant between adjacent spinous processes and compress a second portion of the implant into the adjacent spinous processes.

2. The single instrument of claim 1, wherein the first implant engaging portion comprises an axle extending from the first stationary instrument part to pivotally engage a bore in the pivotal implant part such that the pivotal implant part may pivot about the axis defined by the axle.

3. The single instrument of claim 1, wherein the pivotal implant part further comprises a plurality of compression pads that are adapted to engage an extension of the implant.

4. The single instrument of claim 3, wherein the plurality of compression pads are separated by a cavity, the cavity shaped to cooperatively move over a spacer of the implant.

5. The single instrument of claim 3, wherein the second implant engaging portion comprises a plurality of compression pads that are adapted to engage an extension of the implant and wherein the plurality of compression pads are coupled by a span that is adapted to engage the extension of the implant at approximately the midline.

6. The single instrument of claim 1, wherein the second implant engaging portion comprises a clamp movably coupled thereto, the clamp comprising an end and a ridge extending from the end to form a cavity between the ridge and the second implant engaging portion, wherein the second implant engaging portion is adapted to releasably grasp the implant in the cavity.

7. The single instrument of claim 6, wherein:
   the second implant engaging portion comprises:
   at least one threaded bore, and
   a slot spring coupled to the second implant engaging portion; and the clamp comprises:
   at least one countersunk bore aligned with the threaded bore,
   a compression spring residing in the countersunk bore,
   a fastener having a head and a threaded shaft extending through the compression spring and the countersunk bore, wherein
   the clamp is movably coupled to the second implant engaging portion by cooperatively engaging the fastener with the at least one threaded bore to compress the compression spring in the countersunk bore.

8. The single instrument of claim 7, wherein a force to releasably grasp the implant is provided at least in part by the compression spring and the slot spring.

9. The single instrument of claim 8, wherein the slot spring and the clamp have chamfers to facilitate releasably grasping the implant.

10. The single instrument of claim 1, wherein the first axis extends through a distal end of the stationary instrument part.

11. The single instrument of claim 1, wherein the pivotal implant part is pivotal about an axle extending from a distal end of the stationary instrument part.

12. A single instrument for inserting and compressing a spinous process implant, the instrument comprising:
   a first leg, the first leg comprising a first handle portion and a first implant engaging portion; and
   a second leg, the second leg comprising a second handle portion and a second implant engaging portion, the second leg pivotally coupled to the first leg at a pivot point between the first and second handle portions and the first and second implant engaging portions such that compression of the first and second handle portions causes compression of the first and second implant engaging portions;
   the second implant engaging portion comprising:
   at least one threaded bore,
   a slot spring coupled to the second implant engaging portion, and
   a clamp movably coupled to the second implant engaging portion,
   wherein the first and second implant engaging portions are adapted to couple to an implant and insert a first portion of the implant between adjacent spinous processes and compress a second portion of the implant into the adjacent spinous processes.

13. The single instrument of claim 12, wherein the clamp comprises an end and a ridge extending from the end to form a cavity between the ridge and the second implant engaging portion, wherein the second implant engaging portion is adapted to releasably grasp the implant in the cavity.

14. The single instrument of claim 12, wherein the clamp comprises:
   at least one countersunk bore aligned with the threaded bore,
   a compression spring residing in the countersunk bore, and
   a fastener having a head and a threaded shaft extending through the compression spring and the countersunk bore, and wherein
   the clamp is movably coupled to the second implant engaging portion by cooperatively engaging the fastener with the at least one threaded bore to compress the compression spring in the countersunk bore.

15. The single instrument of claim 12, wherein the first implant engaging portion comprises:
   a stationary instrument part, and
   a pivotal implant part, wherein the pivotal implant part pivots relative to the stationary instrument part in at least one plane.

* * * * *